US00PP33063P2

(12) United States Plant Patent
Hansen

(10) Patent No.: US PP33,063 P2
(45) Date of Patent: May 11, 2021

(54) ***PULMONARIA* PLANT NAMED 'SPOT ON'**

(50) Latin Name: ***Pulmonaria* hybrid**
Varietal Denomination: Spot On

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 16/974,119

(22) Filed: Oct. 7, 2020

(51) Int. Cl.
*A01H 5/02* (2018.01)
*A01H 6/00* (2018.01)

(52) U.S. Cl.
USPC ..... Plt./473

(58) Field of Classification Search
USPC ..... Plt./473
See application file for complete search history.

*Primary Examiner* — Susan McCormick Ewoldt

(57) ABSTRACT

A new and distinct hybrid of Lungwort plant named *Pulmonaria* 'Spot On' characterized by silver spotting on medium green foliage, purplish-pink to salmon-pink flower buds on dense, upright, highly branched stems, that open into purplish-blue campanulate flowers in dense panicles. The new plant has silver spotting on the upper side of both basal and cauline. The plant also show excellent vigor and the foliage has good mildew resistance.

2 Drawing Sheets

Botanical denomination: *Pulmonaria* hybrid.
Variety designation: 'Spot On'.

STATEMENT REGARDING PRIOR DISCLOSURES UNDER 37 CFR 1.77(B)(6)

The first non-enabling public disclosure of the claimed plant, in the form of a photograph and brief description on a website operated by Walters Gardens, Inc. on Dec. 1, 2019. Prior to that, on Oct. 8, 2019, the claimed plant was sold in a private sale by Walters Gardens, Inc. to Corso's Flower and Garden Center. The new plant also was described with a photograph appearing in the "Walters Gardens 2020-2021 Catalog" distributed on May, 20, 2020 with multiple other sales beginning in July 2020. Walters Gardens, Inc. obtained the plant and all information relating thereto, directly from the inventor. No plants of *Pulmonaria* 'Spot On' have been sold in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to a new and distinct cultivar of *Pulmonaria* and given the cultivar name of 'Spot On'. *Pulmonaria* is in the family Boraginaceae. The new cultivar originated from a self-pollination of the unnamed proprietary hybrid with the breeder code 13-125-10 (not patented) on Apr. 15, 2015 at a wholesale perennial nursery in Zeeland, Mich.

The new plant was initially asexually propagated at the same nursery in the summer of 2016 by division of the rhizome and followed by plant tissue culture of the shoot tip. The plant was assigned the breeder code of 15-12-1 through the evaluation process. The original plant and all propagules have shown themselves to be stable and true to type in successive generations of asexual propagation by division at the same nursery in Zeeland, Mich. and also through shoot tip tissue culture.

SUMMARY OF THE INVENTION

The new plant has purplish-red flower buds that can appear nearly salmon pink, and flowers that mature when open to a strong purplish-blue. No comparison with the parent is possible as no plants or photographs were maintained, but the parent was more open, less floriferous, less strongly marked with spots. The nearest comparison plants known to the inventor include: 'Roy Davidson' (not patented), and 'Dark Vader' U.S. Plant Pat. No. 12,333. 'Roy Davidson' has lighter bluish flowers that are more cupped and not as flared, and the habit and foliage are smaller. 'Dark Vader' has a slightly larger habit with shorter flower stems, and the flowers are more pinkish and the foliage is medium-green with more-numerous, smaller, silver spotting.

*Pulmonaria* 'Spot On' is distinct from all other lungwort plants known to the inventor by the following combined traits:

1. Purplish-pink to salmon-pink flower buds open to consistently strong, purplish-blue, campanulate flowers on numerous dense panicles;
2. Medium green foliage with prominent silver spotting on both cauline leaves and basal leaves arising after flowering;
3. Excellent vigor producing compact mounded habit; and
4. Foliage shows good mildew resistance.

BRIEF DESCRIPTION OF THE DRAWING

The photographs of the new plant demonstrate the unique traits of the new plant and the overall appearance. The colors are as accurate as reasonably possible with color reproductions. Variation in ambient light spectrum, source and direction may cause the appearance of minor variation in color.

FIG. 1 shows the spring foliage and flowering habit of the new plant.

FIG. 2 shows a close-up of flowers and buds of the new plant.

FIG. 3 shows the summer foliage of the new plant.

DETAILED PLANT DESCRIPTION

Figure 1:
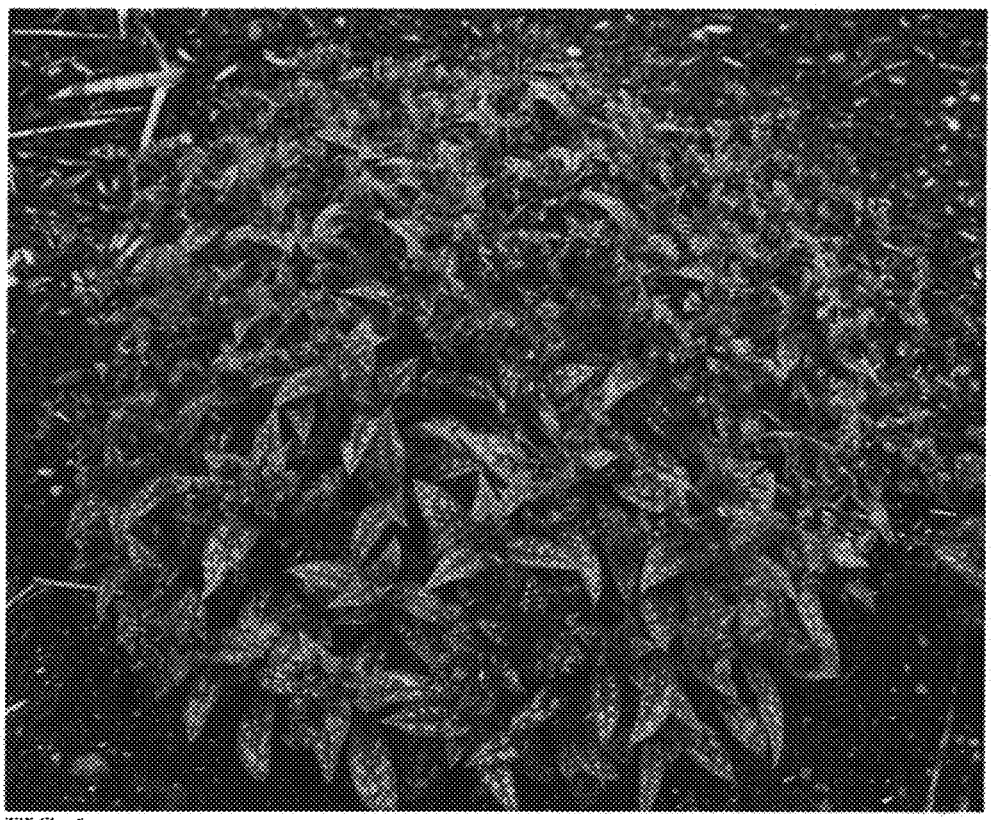
FIG. 1 and FIG. 2 are of a three-year-old plant growing in a partially-shaded garden in Zeeland, Mich.
Figure 2:
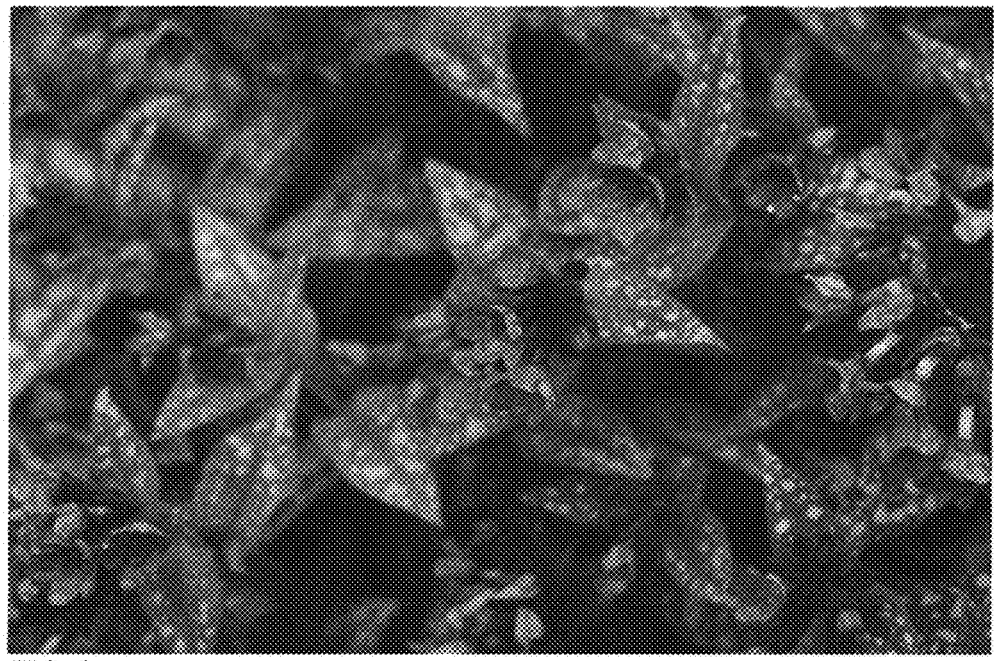
Figure 3:
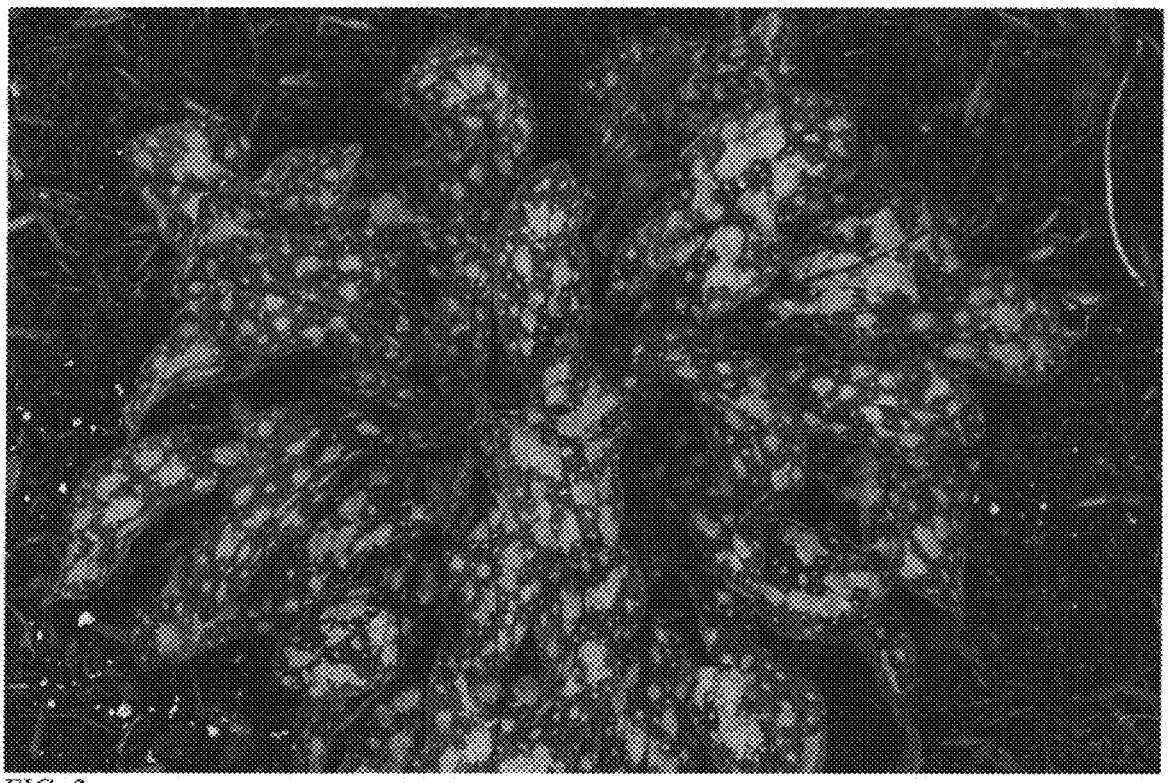
FIG. 3 is of a two-year-old plant in a partially shaded garden in Zeeland, Mich.

The following is a detailed description of a two-year-old plant of 'Spot On' as grown in a partially-shaded greenhouse and a three-year-old plant outdoors in a partially-shaded trial plot at a wholesale nursery in Zeeland, Mich. Plants of the new cultivar have not been tested under all possible conditions. The phenotype may vary with changes in environment, climate, and cultural conditions without change however in the genotype. The color references are in accordance with the 2015 edition of The Royal Horticultural Society Colour Chart except where general color dictionary terms are used.

Parentage: Self-pollination of 13-125-10;

Plant habit: Herbaceous, perennial forming low, multi-stemmed, flowering mound in spring followed in summer producing a clumping basal rosette;

Size: With spring flowering 53.0 cm wide and 30.0 cm tall; summer foliage size to about 75.0 cm wide and 30.0 cm tall;

Vigor: Excellent; produces rooted plantlet in tissue culture in about 14 to 20 days; fills a 3.8 liter container in about 10 weeks from tissue cultured plug;

Propagation: Division of the crown or tissue culture;

Roots: Fleshy, to about 3.0 mm thick; near white depending on soil type, about RHS N155B;

Leaves: In basal rosette; developing prior to cymes dehiscing; simple; oblanceolate; hispid to hispidulous abaxial and adaxial; apex acute; base attenuate, semi-clasping; margin entire, ciliolate; with spots on adaxial surface of between 1.0 and 25.0 mm diameter occasionally converging to about 35.0 mm across;

Leaf size: Basal leaves to about 22.0 cm long and 6.4 cm wide at the center; average about 15.5 cm long and 5.6 cm wide;

Cauline leaf: Alternate; simple; ovate to oblanceolate; hispidulous abaxial and adaxial; acute apex; base attenuate, sessile, clasping; margin ciliolate and entire; with spots on adaxial surface between 1.0 mm and 6.0 mm diameter; to 100.0 mm long and 30.0 mm wide decreasing distally; average about eight cauline leaves per stem below flowers; cauline leaves and stems not persistent, drying after seed production;

Leaf color (basal and cauline): Adaxial nearest RHS 139A with irregular spotted silver portions between RHS 191B and RHS 191C; abaxial between RHS 148B and RHS 147C;

Venation: Pinnate; only abaxial and adaxial midrib distinct; hispid to hispidulous abaxial and adaxial;

Vein color: Adaxial midrib nearest RHS 146D; abaxial midrib between RHS 146C and RHS 146D;

Petiole description: Concavo-convex; scabrous;

Petiole size: To about 15.0 cm long and 10.0 mm wide at base; average about 11.5 cm long and 9.0 mm wide;

Petiole color: Adaxial and abaxial margin nearest RHS 137B; adaxial midrib nearest 145C and basal 35 mm heavily blushed to solid with nearest RHS N186C; abaxial midrib nearest RHS 146D and basal 35 mm heavily blushed to solid with nearest RHS N186C;

Inflorescence: Terminal branched cyme; about 34 cymes per plant with up to 45 flowers per cyme, average 15 flowers per cyme; typically three branches to 45 mm long and 2.0 mm diameter at base; flowering in upper 6 cm and 14 cm across;

Flowering period: Beginning about mid-April and continuing for about four weeks;

Flower longevity: Individual flowers open for about four days;

Flower fragrance: None detected;

Peduncle: Cylindrical; hispidulous; about 34 per plant; about 30 cm long, about 7.0 mm diameter at base; upright;

Peduncle color: Blend between RHS 146D and RHS 145A;

Pedicel: Cylindrical; hirsutulous; 1.0 to 2.0 mm long and about 1.0 mm diameter; color nearest RHS 146D;

Flower bud while petals still tight at apex: Oblong ovoid; to about 14.0 mm long and 4.5 mm wide at petals and calyx about 3.5 mm diameter;

Flower bud color: One day prior to opening calyx nearest RHS 137B, exposed petal nearest RHS 184C;

Flower: Campanulate, actinomorphic, forming funnelform corolla; corolla size about 18.0 mm long and 15.5 mm wide with tube about 8.0 mm long and 3.0 mm diameter;

Petals: Typically five; fused in basal 16.5 mm with rounded apices; margins entire; glabrous abaxial and adaxial except for adaxial ring pubescent with tufts of hairs about 2.0 mm long about 8.0 mm to 9.0 mm from base; about 21.0 mm long and 7.0 mm across at fusion;

Petal color: Young adaxial face nearest blend of RHS 70B and RHS 77B, young abaxial face blend of RHS 70B and RHS 186B, adaxial and abaxial tube nearest RHS NN155A in basal 4.0 mm; mature adaxial face nearest a blend between RHS 94B and RHS 95C with center midrib nearest between RHS 95D and RHS 95C with the corolla tube nearest RNS NN155C and a 2.0 mm wide ring between tube and face blushed with RHS 83A, mature abaxial face nearest a blend between RHS 95C and RHS 94B, corolla tube nearest RHS NN155B with a 2.0 mm thick ring between tube and face nearest RHS 86A; adaxial and abaxial petal faces senescing to nearest RHS 70C before petal drop;

Calyx description: Campanulate; abaxial and adaxial hirsutulous; about 13.0 mm long and 7.0 mm across at apex; adpressed to petals;

Sepals: Five; lanceolate; apices acute; fused in basal 9.0 mm; glabrous adaxial, hirsutulous abaxial; about 13.0 mm long and 3.0 mm across at fusion;

Sepal color: Adaxial nearest RHS 138A; abaxial nearest RHS 137B with tinting of nearest N186C in distal 2.0 mm;

Gynoecium: One; pistil to about 12 mm long;

Ovary: Partially inferior, four-chambered; globose to about 1.0 mm diameter; color nearest RHS 146D;

Style: Cylindrical; glabrous; about 10.0 mm long and about 0.8 mm diameter at base; color nearest RHS 145D;

Stigma: Globose; to about 1.0 mm diameter; color nearest RHS 158B;

Androecium: Five;

Filament: Entirely adnate about 5.0 mm above base of inner corolla; color nearest RHS NN155B;

Anther: Fused to petal; introrse; dorsifixed; longitudinal; oblong about 2.2 mm long and 0.8 mm diameter; color nearest RHS N186B;

Pollen: Abundant; color RHS NN155D;

Seed: To about four per flower, held within calyx; globose with rounded base and acute apex; about 1.0 mm diameter; color nearest RHS N199B;

Resistance to pest and diseases: *Pulmonaria* 'Spot On' has good mildew resistance, but not shown any resistance or susceptibility beyond that common to other lungwort.

Hardiness: The new plant is hardy from at least USDA hardiness zones 3 through 9.

I claim:

1. The new and distinct cultivar of *Pulmonaria* plant named 'Spot On' as herein described and illustrated.

* * * * *